(12) United States Patent
Keim et al.

(10) Patent No.: US 11,357,527 B2
(45) Date of Patent: Jun. 14, 2022

(54) SURGICAL INSTRUMENT FOR MINIMALLY INVASIVE SURGERY

(71) Applicant: avateramedical GmbH, Jena (DE)

(72) Inventors: Tobias Keim, Berlin (DE); Stefan Noack, Berlin (DE)

(73) Assignee: avateramedical GmbH

( * ) Notice: Subject to any disclaimer, the term of this patent is extended or adjusted under 35 U.S.C. 154(b) by 204 days.

(21) Appl. No.: 16/946,050

(22) Filed: Jun. 4, 2020

(65) Prior Publication Data
US 2020/0383696 A1 Dec. 10, 2020

(30) Foreign Application Priority Data
Jun. 4, 2019 (DE) .................. 102019115004.3

(51) Int. Cl.
*A61B 17/29* (2006.01)

(52) U.S. Cl.
CPC ...... *A61B 17/29* (2013.01); *A61B 2017/2902* (2013.01); *A61B 2017/2939* (2013.01)

(58) Field of Classification Search
CPC .... A61B 2017/2927; A61B 2017/2929; A61B 2017/2939; A61B 2017/2926; A61B 2017/2901; A61B 2017/2902; A61B 2017/2932; A61B 17/29
See application file for complete search history.

(56) References Cited

U.S. PATENT DOCUMENTS

| 2008/0097398 | A1 | 4/2008 | Mitelberg |
| 2009/0062602 | A1 | 3/2009 | Rosenberg |
| 2011/0054487 | A1 | 3/2011 | Farnan |
| 2012/0265176 | A1* | 10/2012 | Braun .................. A61B 17/29 606/1 |

FOREIGN PATENT DOCUMENTS

| EP | 2377477 A1 | 5/2012 |
| EP | 2777516 A1 | 9/2014 |

OTHER PUBLICATIONS

European Patent Office, Search Report re Corresponding Application No. 20176985.8, dated Aug. 31, 2020, 7 pages, Germany.

* cited by examiner

*Primary Examiner* — Majid Jamialahmadi
(74) *Attorney, Agent, or Firm* — McGarry Bair PC

(57) ABSTRACT

A surgical instrument for minimally invasive surgery has an instrument shaft with a distal end and a proximal end. The proximal end is connectable to a signal generator. The surgical instrument has an instrument head which is pivotably connected to the distal end of the instrument shaft via a joint, and an end effector which is mounted rotatably about its longitudinal axis in the instrument head. The instrument further comprises a mechanical coupling element which is arranged at least partially in the instrument shaft and is configured to transmit and/or convert mechanical actuating signals of the signal generator for pivoting and rotating the instrument head, as well as a coil spring which bypasses the joint and connects the end effector to the coupling element to rotate the end effector. The coil spring has portions with different spring constants.

15 Claims, 6 Drawing Sheets

SURGICAL INSTRUMENT FOR MINIMALLY INVASIVE SURGERY

CROSS-REFERENCE TO RELATED APPLICATIONS

This application claims priority to Germany application DE 10 2019 115 004.3, filed Jun. 4, 2019.

TECHNICAL FIELD

The invention relates to a surgical instrument for minimally invasive surgery, having an instrument shaft with a distal end and a proximal end. A signal generator is connectable to the proximal end. The surgical instrument has an instrument head which is pivotably connected to the distal end of the instrument shaft via a hinge. Further, the surgical instrument has an end effector which is mounted rotatably about its longitudinal axis in the instrument head. Moreover, the surgical instrument comprises at least one mechanical coupling element which is arranged at least partially in the instrument shaft and is configured to transmit and/or convert mechanical actuation signals of the signal generator for pivoting and rotating the instrument head. A coil spring bypasses the hinge and connects the end effector to the coupling element in order to rotate the end effector. Such an instrument for minimally invasive surgery is, for example, known from document EP 2 377 477 A1.

BACKGROUND

From document EP 3 025 667 A1, a device for robot-assisted surgery is known, in which a surgical instrument is guided with the aid of a manipulator arm of a manipulator and is actuated via a signal generator of the manipulator arm. For this, a coupling unit with drive elements and transmission means is arranged at the distal end of the manipulator arm, and an instrument unit arranged at the distal end of an instrument shaft of the surgical instrument is couplable to the coupling unit via a sterile lock.

In the surgical instrument known from document EP 2 377 477 A1, the coil spring for bypassing the hinge and for connecting the end effector to the coupling element for rotating the end effector is configured and arranged such that the pitch of the spiral spring is adjusted such that in case the spiral spring is maximally bent in accordance with the maximum pivoting position of the instrument head, the spring coils at the inner side of the spring with respect to the bending direction are just in touch with each other or still spaced apart from each other. This has in particular the disadvantage that internal wires, in particular actuating wires or electric conductors, for example, for high-frequency surgery are not safely guided when the coils of the spring do not touch each other or only touch each other in the maximally bent state.

In addition, the instruments known from the prior art have the disadvantage that the spring is bent relatively strongly substantially at one single point in a plane which is orthogonal to the longitudinal axis of the instrument shaft and in which also the axis of rotation of the hinge runs, and the coils in this portion are highly stressed, whereas the adjacent other portions are not bent or bent substantially less.

BRIEF DESCRIPTION

Starting therefrom, there results the object to specify a surgical instrument for minimally invasive surgery which is simply structured and guarantees a safe function.

This object is solved by a surgical instrument for minimally invasive surgery having the features of claim 1. Advantageous developments are specified in the dependent claims.

A surgical instrument for minimally invasive surgery having the features of claim 1 makes it possible to influence the bending behavior of the spring when bending the instrument head. In particular, by selecting suitable spring constants in different portions of the coil spring, an individual adaptation of the bending properties of the spring may be achieved when the distal end of the spring is laterally pivoted away from the longitudinal axis of the instrument shaft. In particular, the shape of the coil spring may be adapted after the distal end of the coil spring has been pivoted away from the longitudinal axis of the instrument shaft, preferably such that a main bending occurs in the center, i.e. in the area of the axis of rotation of the joint. In doing so, the coils are less stressed in the area of the main bending due to a preferably low spring constant as compared to coil springs according to the prior art. With the aid of different spring constants, the coil spring may, however, also be configured such that an area in which the main bending of the spring occurs has a distance to the axis of rotation of the at least one joint in proximal direction or in distal direction.

It is particularly advantageous when, as a result of the spring constants, at least two, in particular three or four, main bending points are formed when bending the instrument head. Such a design is in particular advantageous for a joint that is made up of a plurality of hinges. It is also possible to create a desired bending radius or a desired course of the curve of the longitudinal axis of the spring in portions of the coil spring with the aid of the different spring constants. As a result thereof, it is possible that a force for rotating the instrument head can be transmitted reliably and in particular continuously and without jerks. However, the joint may also be configured as a solid body joint, as it is known from document WO 2006/113216 A2, as a single hinge, as it is known from document EP 2 377 477 A1, and/or as a chain of hinges, as it is known from document EP 2 777 561 B1.

When at least one actuating wire and/or an electrically conductive wire is guided inside the coil spring, these may safely be guided due to the easily adaptable bending shape of the coil spring also when pivoting the instrument head and the associated lateral deflection or bending of the coil spring so that damage to these wires can be avoided.

It is particularly advantageous when the spring constant decreases from the distal end of the coil spring and from the proximal end of the coil spring, preferably continuously, in particular uniformly, toward the center or toward a central area with a constant spring constant of the coil spring, or increases toward this area continuously, in particular uniformly. As a result, a main bending in the center of the spring may be achieved.

Further, it is advantageous when the coil of the coil spring has a rectangular cross-section. As a result, high spring constants with little installation space may be achieved. In addition, when a rotary motion is transmitted via the coil spring about the longitudinal axis of the coil spring, only a slight elastic deformation of the spring occurs so that an easy operability of the end effector is possible. Moreover, such a coil spring may be produced easily by mechanical machining processes such as milling and winding, or alternatively with the aid of a 3D printer.

Further, it is advantageous when the coil of the coil spring has a different cross-sectional area in the portions with different spring constants. By changing the cross-sectional area in amount and/or shape, the spring constant may even be different in portions of the coil spring when the entire coil spring is made of the same material. In addition, the spring constant by changing the cross-sectional area may also be combined in connection with other measures for forming different spring constants in portions of the coil spring.

Further, it is advantageous when the coil of the coil spring has a different pitch in the portions with different spring constants. This enables an easy production of a coil spring with portions having different spring constants.

Further, it is advantageous when the coil of the coil spring has sections with materials with different moduli of elasticity. As a result, the different spring constants may be provided in the portions simply by the fact that these portions of the coil spring are made of different materials. This is particularly easily possible when several spring segments are put together to one total coil spring in that the coils of the portions are welded or glued together or are connected otherwise. Alternatively, the different materials may also be used successively in a 3D print for producing the spring. Here a continuous transition between different materials or material configurations is also conceivable.

It is particularly advantageous when the coil spring is a linear spring. Then, the coil spring is preferably designed such that when force is applied in the direction of the central axis of the coil spring, the spring deforms uniformly, i.e. in a manner linear to the force, with increasing force. Here, however, a different deformation occurs in each of the portions with different spring constants.

Further, it is advantageous when the coupling element comprises a rotating tube shaft, when the proximal end of the coil spring is connected to the rotating tube shaft in a rotationally fixed manner, and when the rotating tube shaft is mounted rotatably in the instrument shaft. This enables a simple and compact arrangement of the components of the coupling element inside the instrument shaft, the rotating tube shaft offering a safe drive possibility having a low torsion in the direction of rotation for rotating the instrument head or the end effector.

In an alternative embodiment, the coil spring is arranged between the rotating tube shaft and the instrument head in a biased manner. As a result, the torsion properties of the coil spring may be adapted further. Further, it is advantageous when the coil spring is configured and arranged such that from a predetermined pivot position of the instrument head when pivoting the instrument head, the coils of the coil spring come into contact at the inner side of the coil spring with respect to the bending direction, and that when pivoting the instrument head beyond the predetermined pivot position up to a maximum pivot position of the instrument head, the coils of the coil spring press against each other with a press-on force at the inner side of the spring with respect to the bending direction. In the maximum pivot position of the instrument head, the coils of the coil spring may have a larger distance at the outer side of the spring as compared to their initial position with a straight instrument head, i.e. when the instrument head is not pivoted about the axis of rotation of the joint. Due to the increased distance at the outer side of the spring, the coils are pulled apart thereat at least in the maximum pivot position. As a result, it is guaranteed that from the contact in the predetermined pivot position up to the maximum pivot position the coils at the inner side always contact each other and wires or cables guided inside the coil spring are safely guided with low friction on the inner side of the spring so that damage to these wires is avoided.

Further, it is advantageous when the instrument head is pivotable about an axis of rotation by a predetermined angle with the aid of the coupling element, the axis of rotation being orthogonal to the longitudinal axis of the instrument shaft. As a result, a simple design and arrangement of the joint is possible. The joint may be formed as a simple hinge. Here, it is particularly advantageous when the pivoting of the instrument head is performed by a translatory motion of an inner shaft along its longitudinal axis, which inner shaft is arranged between the instrument shaft and the rotating tube shaft. As a result, an easy and reliable coupling of the coupling element to the instrument head is possible to enable both a pivoting of the entire instrument head and a rotary motion of the end effector and/or the instrument head in a reliable manner.

It is particularly advantageous when the axis of rotation of the joint runs through and orthogonal to the longitudinal axis of the coil spring. As a result, a simple and compact structure of the instrument in the area of the instrument head and of the transition between the instrument shaft and the instrument head is possible.

It is particularly advantageous when the coil spring does not deform or only slightly deforms in the direction of rotation of the coil spring for rotating the instrument head or the end effector when exerting normal forces required for rotation of the instrument head. This enables an easy and safe actuation of the surgical instrument. In particular, a safe handling of the surgical instrument is guaranteed since a desired initiated rotary motion is transmitted relatively accurately via the coil spring.

Further, it is advantageous when the signal generator connected to the proximal end of the instrument shaft is a manual actuating unit and/or a coupling element for coupling the surgical element to at least one drive unit of a manipulator arm of a manipulator. As a result, the surgical instrument may be easily and safely actuated.

The surgical instrument preferably comprises at least one end effector arranged at the instrument head and insertable into a body opening of a patient, such as a clamp, scissors, a gripper, a needle holder, a microdissector, a clamping device, a stapling device, a rinsing and/or suction device, a cutting blade, a cauterization probe, a catheter and/or a suction nozzle or an end effector for high-frequency surgery. As a result, the surgical instrument may optionally have different end effectors which may be used for common minimally invasive surgeries, in particular in the laparoscopic surgery. However, also other surgical instruments may be used additionally or alternatively.

Hereinafter, further features and advantages are described on the basis of embodiments in connection with the enclosed Figures.

DETAILED DESCRIPTION

Figure 1:
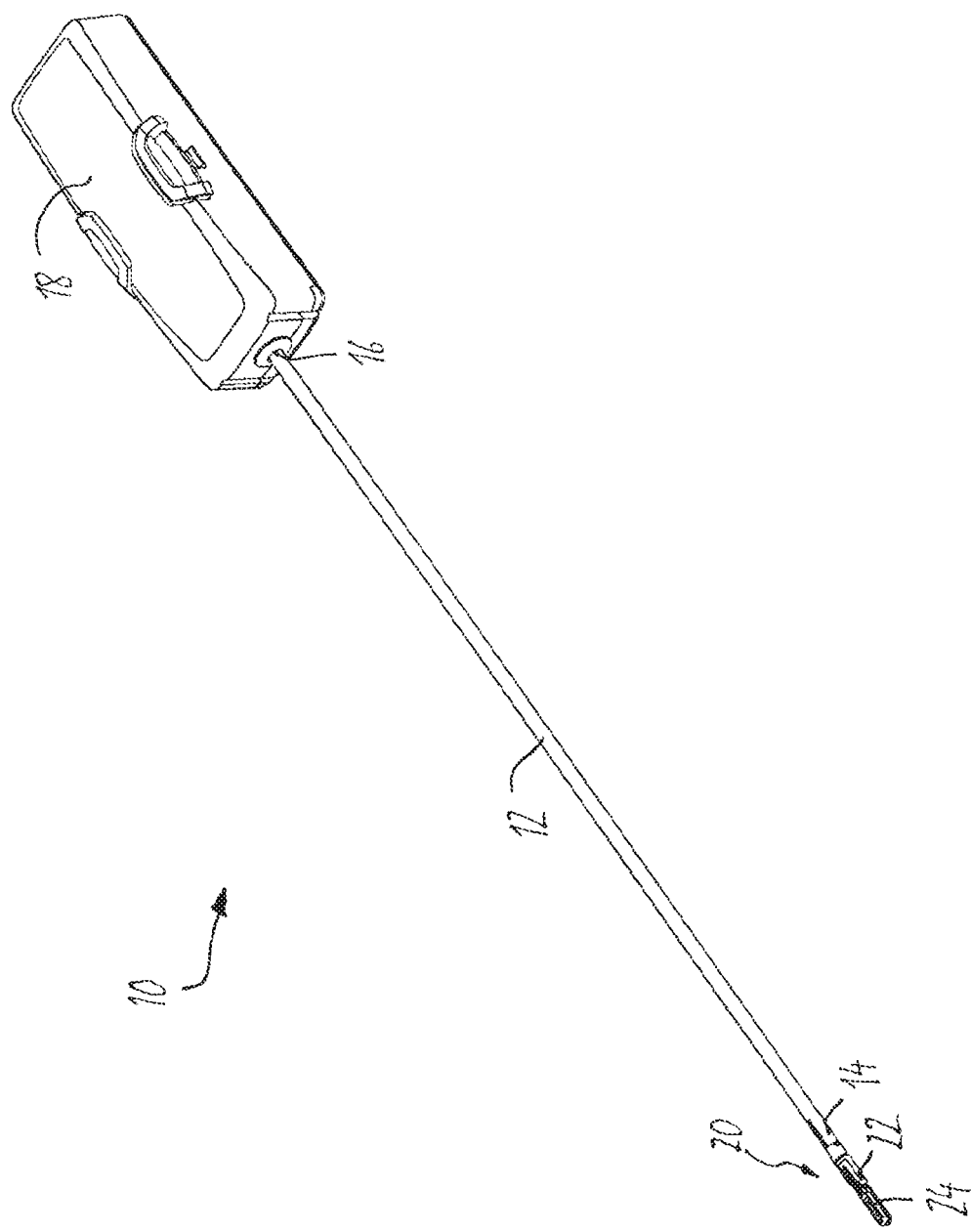
FIG. 1 shows a perspective illustration of a surgical instrument for minimally invasive surgery for use with a manipulator.

FIG. 1 shows a surgical instrument 10 for minimally invasive surgery. This instrument 10 has an instrument shaft 12 with a distal end 14 and a proximal end 16. The proximal end 16 of the instrument shaft 12 is connected to an instrument unit 18. Via the instrument unit 18, the surgical instrument 10 is connectable to a coupling unit of a manipulator arm of a manipulator. Such manipulators are also referred to as telemanipulator systems and serve for robot-assisted surgery. Such manipulators are in particular disclosed in documents EP 3 025 667 A1 and WO 2016/083189 A1. The inventive solution may also be used for laparoscopic hand instruments without any changes.

The surgical instrument 10 has an instrument head 20 connected to the distal end 14 of the instrument shaft 12 via a joint formed as a hinge 22. The instrument head 20 comprises an end effector 24 which is mounted rotatably about its longitudinal axis at the instrument head 20.

Figure 2:
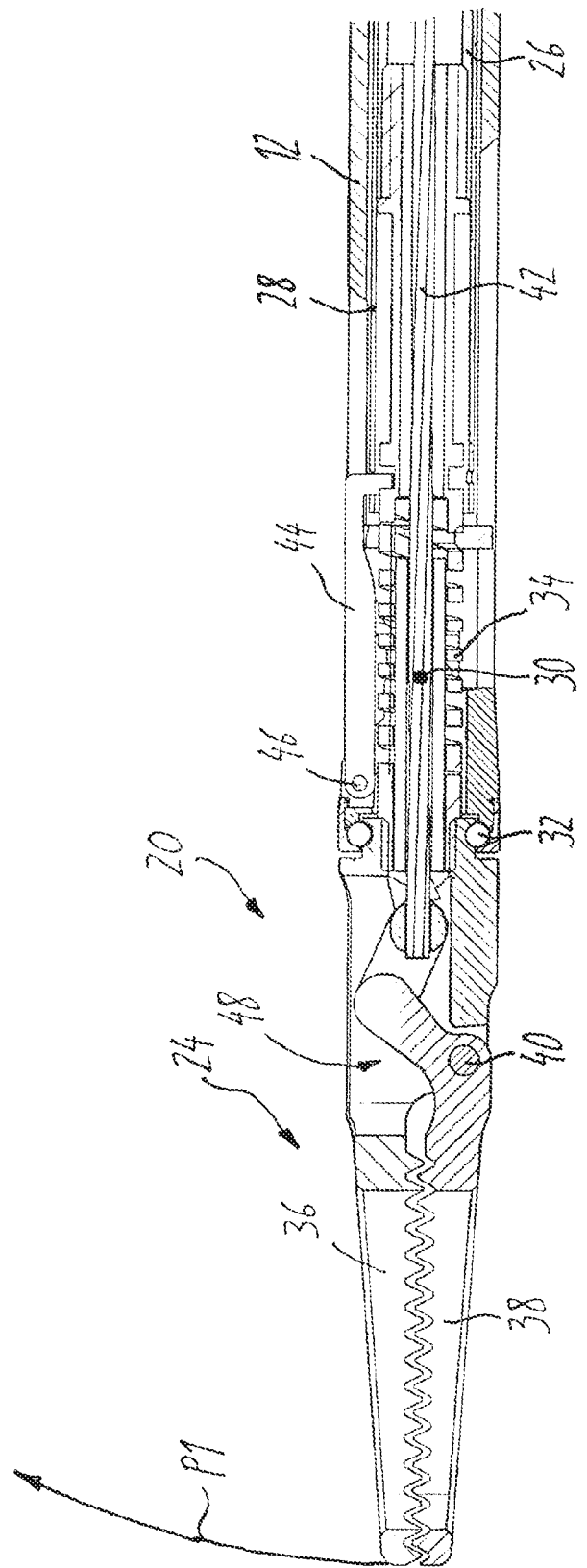
FIG. 2 shows a sectional illustration of a distal portion of the instrument of FIG. 1.

FIG. 2 shows a sectional illustration of a distal portion of the surgical instrument 10 according to FIG. 1. Inside the instrument shaft 12, a rotating tube shaft 26 mounted rotatably relative to the instrument shaft 12 and an inner shaft 28 arranged between the rotating tube shaft 26 and the instrument shaft 12 is arranged, wherein the inner shaft 28 may be moved at least in longitudinal direction of the instrument shaft 12 to pivot the instrument head 20 about an axis of rotation 30 in the direction of the arrow P1, which axis of rotation 30 runs orthogonal to the drawing plane and is additionally entered in FIG. 2. The arrow P1 thus indicates the pivot direction of the instrument head 20, into which it can be moved from the rest position shown in FIG. 2. The maximum angle about which the instrument head 20 may be pivoted in the direction of the arrow P1 is usually in a range between 60° and 90°, preferably at 65° or at 70°. In other embodiments, also other joints may be used instead of the hinge 22.

The instrument head 20 is rotatable via a ball bearing 32 about the longitudinal axis of the instrument shaft 12 in the rest position shown in FIG. 2. So that the instrument head 20 may also be rotated in the case of an instrument head 20 pivoted about the axis of rotation 30, a coil spring 34 is provided between the rotating tube shaft 26 and the instrument head 20 for transmitting the rotary motion, the proximal end of the coil spring being connected to the rotating tube shaft 26 in a rotationally fixed manner and the distal end of which being connected to the proximal end of the instrument head 20 in a rotationally fixed manner. The coil spring 34 is arranged inside the hinge 22 and bypasses the same. The end effector 24 has a first jaw part 36 and a second jaw part 38. The first jaw part 36 is rigidly connected to the instrument head 20. The second jaw part is arranged pivotably about the pivot axis defined by the pin 40 so that the gripper formed by the first jaw part 36 and the second jaw part 38 may be opened and closed by pivoting the second jaw part 38 about the pin 40. A pivoting of the jaw part 38 about the axis of rotation formed by the pin 40 is controlled by an actuating wire 42 and an actuating mechanism 48, the actuating wire 42 performing a pushing movement in the direction of the distal end for opening the gripper and being pulled to the proximal end for closing the gripper. The actuating wire 42 extends inside the coil spring 34 through the same so that also when the instrument head 20 is pivoted, an actuation of the end effector 24 or an actuation of the gripper is possible. In other embodiments, the second jaw part 38 is likewise configured movably.

In the end effector 24 or in other end effectors, additionally an electrical connection to the end effector 24 can be established via the actuating wire 42 in order to use the end effector 24 or the surgical instrument 10 for high-frequency surgery.

The inner shaft 28 is connected to the proximal end of a pulling lever 44. The pulling lever 44 is articulated to the instrument head 20 so as to be pivotable about a pivot axis 46. By a movement of the proximal end of the pulling lever 44 in the direction of the proximal end of the instrument shaft 12, which movement is initiated by the inner shaft 28, the instrument head is pivoted about the axis of rotation 30 of the hinge 22 and the coil spring 34 is bent laterally.

Figure 3:
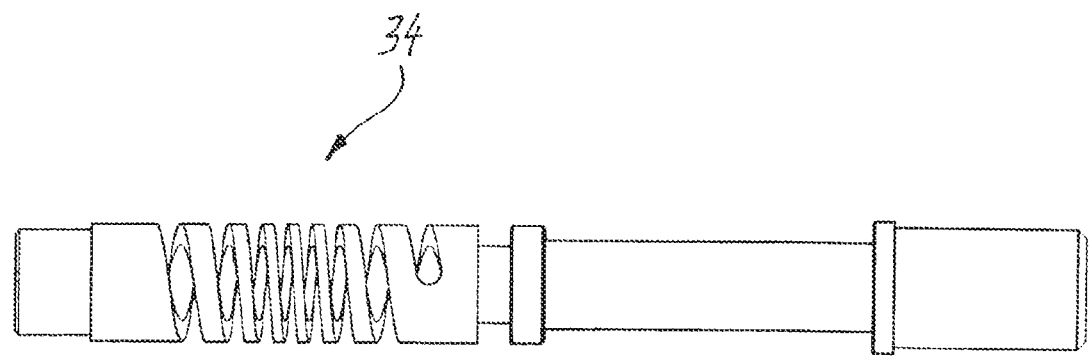
FIG. 3 shows a coil spring inserted in the instrument of FIGS. 1 and 2 for transmitting a rotary motion.

FIG. 3 shows the spring 24 of FIG. 2 in a biased state, with which the coil spring 24 is arranged in the surgical instrument 10. The coil spring 34 is made of spring steel, the cross-sectional surface of the coils decreasing from the proximal end of the coil spring 34 and from the distal end of the coil spring 34 toward the center of the coil spring 34 so that the spring constant decreases from the proximal and from the distal end of the coil spring 34, respectively. The pitch of the coil spring 34 in the unbiased state and/or in the biased state is preferably constant. In other embodiments, additionally or alternatively to influencing and changing the spring constant over the length of the coil spring 34, the pitch of the coils may be different or the spring properties of the material in sections of the coils may be different. This may in particular be done by assembling the coil spring 34 from different coil sections. Alternatively or additionally, individual coil sections may be partially hardened.

Figure 4:
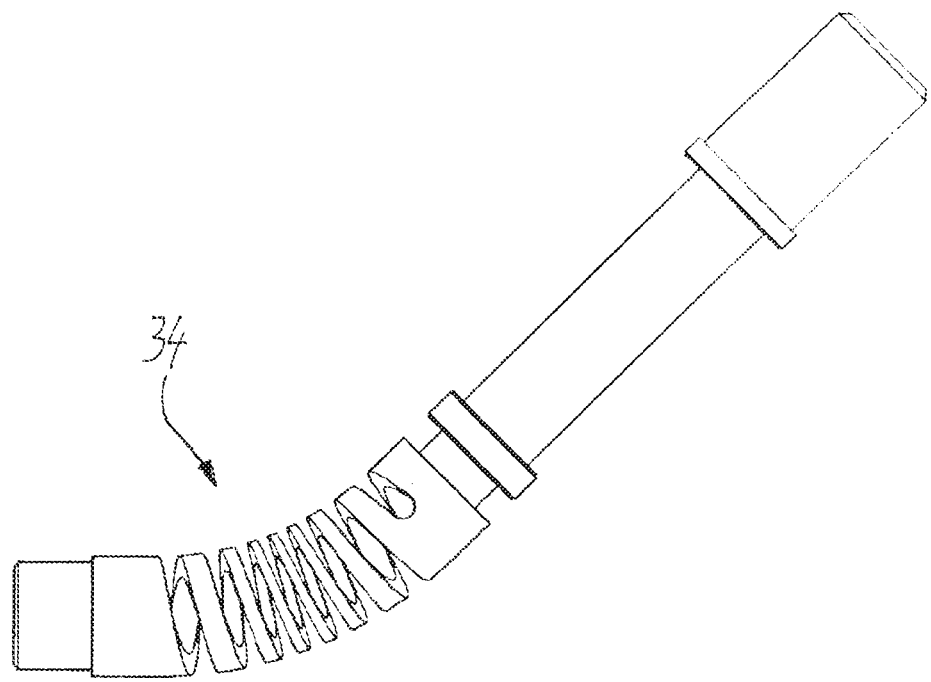
FIG. 4 shows the coil spring of FIG. 3 in a state bent by 45°.

FIG. 4 shows the spring of FIG. 3 in a state after pivoting the instrument head 20 relative to the instrument shaft 28 by an angle of about 45°, wherein a longitudinal axis of the instrument head and the longitudinal axis of the instrument shaft span an angle of 135°.

Figure 5:
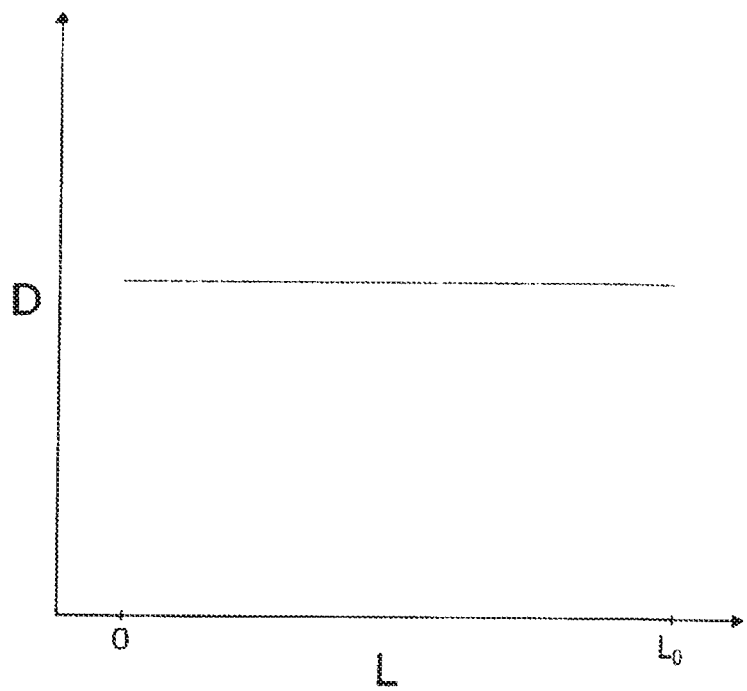
FIG. 5 shows a diagram illustrating the curve of the spring constant D over the length of a coil spring according to the prior art.

FIG. 5 shows the curve of the spring constant D over the length L of a coil spring, wherein zero is the proximal end of the coil spring and L0 is the distal end of the coil spring. The coil spring of FIG. 5 is a coil spring with a constant spring constant D, as used in surgical instruments of the prior art.

Figure 6:
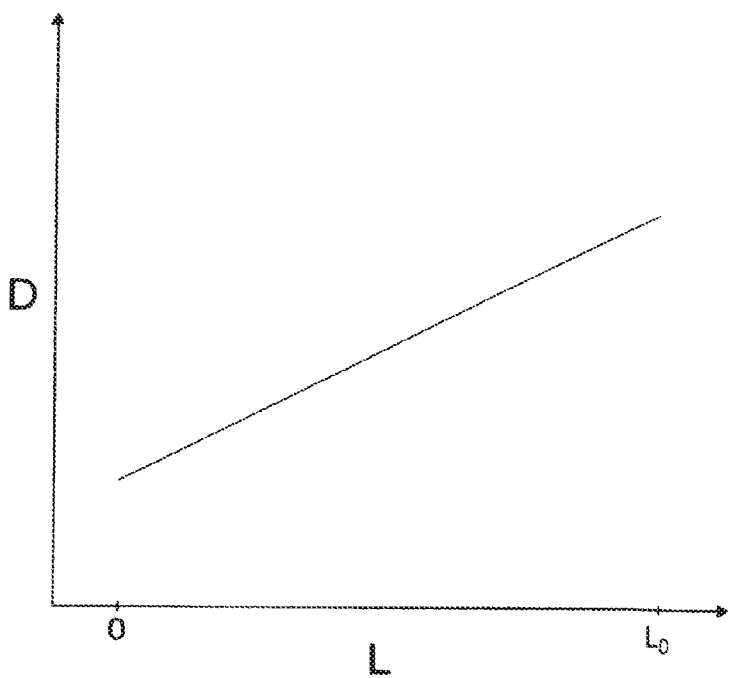
FIG. 6 shows a diagram illustrating the curve of the spring constant D over the length L of the coil spring according to a first embodiment.

FIG. 6 shows the curve of the spring constant D over the length of the coil spring 34 according to a first embodiment. Here, the spring constant D continuously increases from the proximal end of the coil spring 34 to the distal end of the coil spring 34. This can be achieved, for example, in that the cross-section of the coils likewise continuously increases from the proximal end to the distal end of the coil spring 34.

Figure 7:
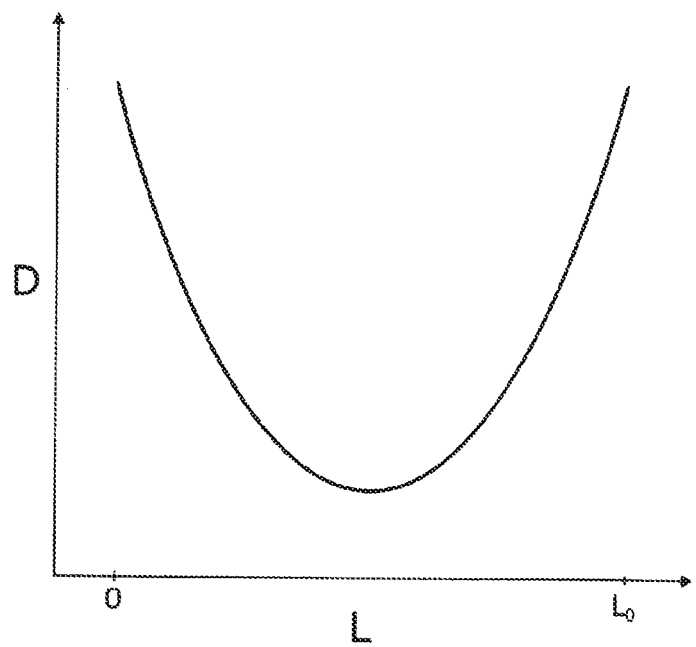
FIG. 7 shows a diagram illustrating the curve of the spring constant D over the length L of the coil spring according to a second embodiment.

FIG. 7 shows a curve of the spring constant D over the length L of the coil spring 34 according to a second embodiment. The curve of the spring constant D shown in FIG. 7 is the curve of the spring constant D caused by the change in cross-section of the coil spring 34 of FIGS. 2 to 4, when the coil spring 34 has a constant pitch and constant material properties over the entire length of the coil spring 34.

Figure 8:
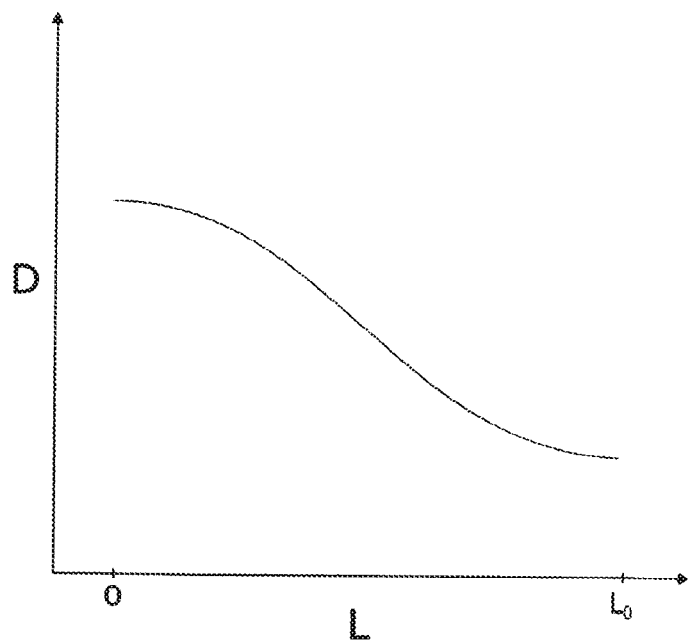
FIG. 8 shows a diagram illustrating the curve of the spring constant D over the length L of the coil spring according to a third embodiment.

FIG. 8 shows the curve of the spring constant D over the length of a coil spring 34 according to a third embodiment. Here, the spring constant does not linearly decrease from the proximal end to the distal end.

Figure 9:
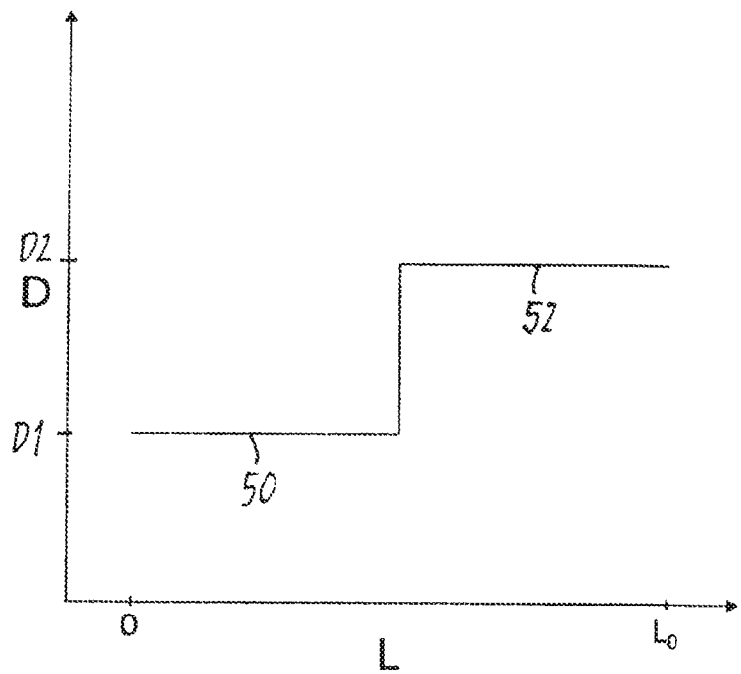
FIG. 9 shows a diagram illustrating the curve of the spring constant D over the length L of the coil spring according to a fourth embodiment.

FIG. 9 shows the curve of the spring constant D over the length L of the coil spring 34 according to a fourth embodiment. The coil spring 34 has a first portion 50 with a constant spring constant D1 and a second portion 52 with a constant spring constant D2. Such a curve of the spring constant D is, for example, achieved by a stepped cross-sectional change of the coil of the coil spring 34 and/or by different materials in the two portions 50, 52 with constant spring constants D1, D2, wherein the portions 50, 52 with different materials are connected to each other in the center of the coil spring 34, i.e. at the stepped transition between low spring constant D1 and high spring constant D2.

Figure 10:
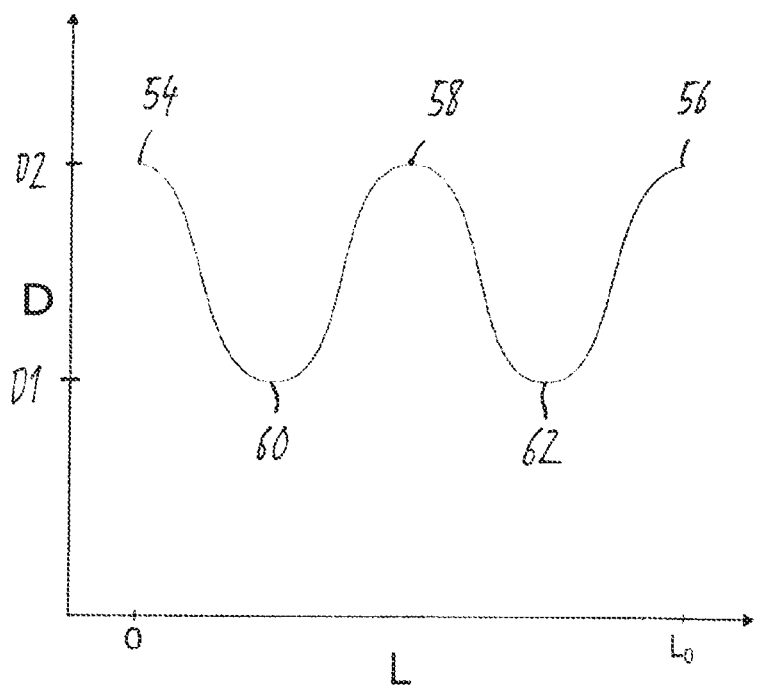
FIG. 10 shows a diagram illustrating the curve of the spring constant D over the length L of the coil spring according to a fifth embodiment.

FIG. 10 shows the curve of the spring constant D over the length of a coil spring 34 according to a fifth embodiment. In the shown curve, the spring constant D of the coil spring 34 is high at the distal end 54 and the proximal end 56 as well as in the center 58, wherein between the distal end 54 and the center 58 and between the center 58 and the proximal end 56 each time a minimum 60, 62 of the spring constant D is achieved. The curve shown in FIG. 10 has the consequence that in the portions 60, 62 with a minimum spring constant D a high bending occurs when pivoting the instrument head 20, and in the portions 54, 56, 58 with a high spring constant a smaller deformation occurs.

As shown in FIGS. 6 to 10, by means of the portions with different spring constants an individual adaptation of the torsion and bending properties of the coil spring 34 can be achieved when pivoting the instrument head 20. In particular, the spring constant D can be varied such over the length of the coil spring 34 that the main bending area lies in the center, i.e. in the area of the axis of rotation 30 of the hinge 22, or not in the center, i.e. in front of or behind the axis of rotation 30 of the hinge 22, wherein one, two, three or four bending points may be provided. By a mutual contact of the coils of the coil spring 34 when pivoting the instrument head 20 a stabilization of the internal wires 42 is achieved.

Coil springs 34 with portions with different spring constants D can be produced in particular by winding, machining, laser cutting, 3D printing, welding, gluing and other suitable production methods. The variation of the spring constant D over the length L of the coil spring 34 is caused in particular by a change of the cross-section of the coil, by a different pitch of the coil of the coil spring 34, by different materials and/or material gradients, by partially hardening or another suitable choice of the spring configuration. By the suitable variation of the spring constant D over the length of the coil spring 34, in particular the torsion stiffness of the coil spring 34 and the behavior of the coil spring 34 when bending the instrument head 20 can be influenced.

The invention claimed is:

1. A surgical instrument for minimally invasive surgery, with an instrument shaft with a distal end and a proximal end to which a signal generator is connectable,
with an instrument head which is pivotably connected to the distal end of the instrument shaft via at least one joint,
with an end effector which is mounted rotatably about its longitudinal axis in the instrument head,
with at least one mechanical coupling element which is arranged at least partially in the instrument shaft and is configured to transmit and/or convert mechanical actuating signals of the signal generator for pivoting and rotating the instrument head,
a coil spring which bypasses the at least one joint and connects the end effector to the at least one mechanical coupling element to rotate the end effector, characterized in that
the coil spring has portions with different spring constants.

2. The device according to claim 1, characterized in that the spring constant decreases from a distal end of the coil spring and from a proximal end of the coil spring uniformly toward or to a central area of the coil spring.

3. The device according to claim 1, characterized in that a coil of the coil spring has a rectangular cross-section.

4. The device according to claim 1, characterized in that a coil of the coil spring has different cross-sectional areas in the portions with different spring constants.

5. The device according to claim 1, characterized in that a coil of the coil spring has different pitches in the portions with different spring constants.

6. The device according to claim 1, characterized in that a coil of the coil spring has materials with different moduli of elasticity in the portions with different spring constants.

7. The device according to claim 1, characterized in that the coil spring is a linear spring.

8. The device according to claim 1, characterized in that the coupling element comprises a rotating tube shaft, that a proximal end of the coil spring is connected to the rotating tube shaft in a rotationally fixed manner, and that the rotating tube shaft is mounted rotatably in the instrument shaft.

9. The device according to claim 8, characterized in that the coil spring is arranged between the rotating tube shaft and the instrument head in a biased manner.

10. The device according to claim 1, characterized in that the coil spring is configured and arranged such that coils of the coil spring, from a predetermined pivot position of the instrument head when pivoting the instrument head, come into contact at an inner side of the coil spring with respect to a bending direction, and that the coils of the coil spring when pivoting the instrument head into a maximum pivot position of the instrument head press against each other with a press-on force on the inner side of the coil spring with respect to the bending direction, wherein on an outer side of the coil spring the distance of the coils to each other is increased as compared to an initial position.

11. The device according to claim 1, characterized in that the instrument head is pivotable about an axis of rotation by a predetermined angle with the aid of the at least one mechanical coupling element, wherein the axis of rotation is orthogonal to a longitudinal axis of the instrument shaft.

12. The device according to claim 11, characterized in that the pivoting of the instrument head is caused by a translatory motion of an inner shaft along its longitudinal axis, which the inner shaft is arranged between the instrument shaft and a rotating tube shaft.

13. The device according to claim 11, characterized in that the axis of rotation of the at least one joint runs through at least one of orthogonal to a longitudinal axis of the coil spring and in a plane of the coil spring that is orthogonal to the longitudinal axis of the coil spring.

14. The device according to claim 1, characterized in that the coil spring is designed in a torsionally stiff manner.

15. The device according to claim 1, characterized in that the signal generator connected to the proximal end of the instrument shaft is a manual actuating unit and/or a coupling element for coupling the surgical instrument to at least one drive unit of a manipulator arm of a manipulator.

* * * * *

UNITED STATES PATENT AND TRADEMARK OFFICE
CERTIFICATE OF CORRECTION

PATENT NO.        : 11,357,527 B2
APPLICATION NO.   : 16/946050
DATED             : June 14, 2022
INVENTOR(S)       : Tobias Keim and Stefan Noack It is certified that error appears in the above-identified patent and that said Letters Patent is hereby corrected as shown below:

In the Claims

Claim 8, reads:
"The device according to claim 1, characterized in that the coupling element comprises a rotating tube shaft, that a proximal end of the coil spring is connected to the rotating tube shaft in a rotationally fixed manner, and that the rotating tube shaft is mounted rotatably in the instrument shaft."

Should read:
"The device according to claim 1, characterized in that the at least one mechanical coupling element comprises a rotating tube shaft, that a proximal end of the coil spring is connected to the rotating tube shaft in a rotationally fixed manner, and that the rotating tube shaft is mounted rotatably in the instrument shaft."

Signed and Sealed this
Sixteenth Day of August, 2022

Katherine Kelly Vidal
*Director of the United States Patent and Trademark Office*